United States Patent
Buscemi

(12) 
(10) Patent No.: US 8,517,028 B2
(45) Date of Patent: Aug. 27, 2013

(54) STIFFENING PROCEDURE FOR SLEEP APNEA

(75) Inventor: Paul J. Buscemi, Long Lake, MN (US)

(73) Assignee: Medtronic Xomed, Inc., Jacksonville, FL (US)

(*) Notice: Subject to any disclaimer, the term of this patent is extended or adjusted under 35 U.S.C. 154(b) by 1372 days.

(21) Appl. No.: 11/426,133

(22) Filed: Jun. 23, 2006

(65) Prior Publication Data

US 2007/0295340 A1  Dec. 27, 2007

(51) Int. Cl.
*A61F 5/56* (2006.01)
*A61F 2/02* (2006.01)

(52) U.S. Cl.
USPC .................. 128/848; 602/902; 623/23.73

(58) Field of Classification Search
USPC ............... 128/848, 897; 602/902; 623/23.73
See application file for complete search history.

(56) References Cited

U.S. PATENT DOCUMENTS

| | | | |
|---|---|---|---|
| 5,843,021 A | 12/1998 | Edwards et al. | |
| 5,988,171 A | 11/1999 | Sohn et al. | |
| 6,161,541 A | 12/2000 | Woodson | |
| 6,250,307 B1 | 6/2001 | Conrad et al. | |
| 6,431,174 B1* | 8/2002 | Knudson et al. | 128/898 |
| 6,513,530 B2 | 2/2003 | Knudson et al. | |
| 6,523,542 B2 | 2/2003 | Knudson et al. | |
| 6,601,584 B2 | 8/2003 | Knudson et al. | |
| 7,337,781 B2 | 3/2008 | Vassallo | |
| 2004/0139975 A1* | 7/2004 | Nelson et al. | 128/848 |
| 2004/0149290 A1 | 8/2004 | Nelson et al. | |
| 2005/0092332 A1 | 5/2005 | Conrad et al. | |
| 2005/0092334 A1* | 5/2005 | Conrad et al. | 128/898 |
| 2005/0126563 A1* | 6/2005 | van der Burg et al. | 128/200.24 |
| 2005/0199248 A1 | 9/2005 | Pflueger et al. | |
| 2006/0201519 A1* | 9/2006 | Frazier et al. | 128/848 |
| 2006/0235380 A1 | 10/2006 | Vassallo | |

FOREIGN PATENT DOCUMENTS

| | | |
|---|---|---|
| DE | 199 20 114 A1 | 11/2000 |
| EP | 1039859 B1 | 12/1998 |
| WO | WO 2005/082452 A1 | 9/2005 |
| WO | WO 2006/072571 A1 | 7/2006 |

OTHER PUBLICATIONS

Eisle et al., "Direct Hypoglossal Nerve Stimulation in Obstructive Sleep Apnea", *Arch. Otolaryngol. Head Neck Surg.*, vol. 123, pp. 57-61 (1997).
Miller et al., "Role of the tongue base suspension suture with The Repose System bone screw in the multilevel surgical management of obstructive sleep apnea", *Otolaryngol. Head Neck Surg.*, vol. 126, pp. 392-398 (2002).
Powell et al., "Radiofrequency tongue base reduction in sleep-disordered breathing: A pilot study", *Otolaryngol Head Neck Surg.*, vol. 120, pp. 656-664 (1999).
Powell et al., "Radiofrequency Volumetric Reduction of the Tongue—A Porcine Pilot Study for the Treatment of Obstructive Sleep Apnea Syndrome", *Chest*, vol. 111, pp. 1348-1355 (1997).
U.S. Appl. No. 11/107,160, filed Apr. 15, 2005.
U.S. Appl. No. 11/107,161, filed Apr. 15, 2005.

* cited by examiner

*Primary Examiner* — Patricia Bianco
*Assistant Examiner* — Tarla Patel
(74) *Attorney, Agent, or Firm* — Merchant & Gould P.C.

(57) ABSTRACT

A patient's obstructive sleep apnea is treated by placing a fibrosis-inducing agent is placed within the tongue in a region extending substantially from a hyoid bone rearward toward a back surface of the tongue and upwardly along the back wall toward a free end of a soft palate of the patient.

1 Claim, 6 Drawing Sheets ized U.S. Pat. No. 8,517,028 B2

STIFFENING PROCEDURE FOR SLEEP APNEA

I. BACKGROUND OF THE INVENTION

1. Field of the Invention

This invention pertains to a method for treating a condition of an upper airway of a patient. More particularly, this invention is directed to a method for treating obstructive sleep apnea by stiffening a region of a tongue of a patient.

2. Description of the Prior Art

Upper airway conditions such as obstructive sleep apnea ("OSA") and snoring have received a great deal of attention. These conditions have recognized sociological and health implications for both the patient and the patient's bed partner.

Numerous attempts have been made towards treating OSA and snoring. These include placing implants in either the tissue of the soft palate or the pharyngeal airway as disclosed in commonly assigned U.S. Pat. No. 6,250,307 to Conrad et al. dated Jun. 26, 2003, U.S. Pat. No. 6,523,542 to Metzger et al. dated Feb. 25, 2003 and U.S. Pat. No. 6,431,174 to Knudson et al. dated Aug. 13, 2002. Further, U.S. Pat. No. 6,601,584 to Knudson et al. dated Aug. 5, 2003 teaches a contracting implant for placement in the soft palate of the patient.

Another prior art technique for treating OSA or snoring is disclosed in U.S. Pat. No. 5,988,171 to Sohn et al. dated Nov. 23, 1999. In the '171 patent, a cord (e.g., a suture material) (element 32 in FIG. 6 of the '171 patent) is placed surrounding a base of the tongue and secured to the jaw by reason at an attachment member (element 20 in FIG. 6 of the '171 patent). In the method of the '171 patent, the member 32 can be shortened to draw the base of the tongue toward the jaw and thereby move the tissue of the base of the tongue away from the opposing tissue of the pharyngeal airway. However, this procedure is often uncomfortable. This procedure, referred to as tongue suspension, is also described in Miller et al., "Role of the tongue base suspension suture with The Repose System bone screw in the multilevel surgical management of obstructive sleep apnea", *Otolaryngol. Head Neck Surg.*, Vol. 126, pp. 392-398 (2002).

Another technique for debulking tissue includes applying radio frequency ablation to either the tongue base or of the soft palate to debulk the tissue of the tongue or palate, respectively. This technique is illustrated in U.S. Pat. No. 5,843,021 to Edwards et al. dated Dec. 1, 1998. RF tongue base reduction procedures are described in Powell et al., "Radiofrequency tongue base reduction in sleep-disordered breathing: A pilot study", *Otolaryngol. Head Neck Surg.*, Vol. 120, pp. 656-664 (1999) and Powell et al., "Radiofrequency Volumetric Reduction of the Tongue—A Porcine Pilot Study for the Treatment of Obstructive Sleep Apnea Syndrome", *Chest*, Vol. 111, pp. 1348-1355 (1997).

A surgical hyoid expansion to treat OSA is disclosed in U.S. Pat. No. 6,161,541 to Woodson dated Dec. 19, 2000. Other tongue treatments for OSA include stimulation of the hypoglossal nerve. This procedure is described in Eisle et al., "Direct Hypoglossal Nerve Stimulation in Obstructive Sleep Apnea", *Arch. Otolaryngol. Head Neck Surg.*, Vol. 123, pp. 57-61 (1997).

Commonly assigned U.S. patent application Publication Nos. US 2005/0092332 A1 and US 2005/0092334 A1 (both published May 5, 2005) describe tongue-based treatments to treat obstructive sleep apnea. U.S. patent application Ser. Nos. 11/107,160 and 11/107,161 (both filed Apr. 15, 2005 and assigned to the assignee of the present invention) describe various implants for a tongue to treat obstructive sleep apnea.

European Patent EP 1,039,859 B1 granted Dec. 3, 2003 describes a brace placed in the tongue. German Patent No. 19 920 114 describes struts in pharyngeal wall. U.S. patent application Publication Nos. US 2005/0126563 A1 published Jun. 16, 2005 and US 2005/0199248 A1 published Sep. 15, 2005 describe stents in airway. U.S. patent application Publication Nos. US 2004/0139975 published Jul. 22, 2004 and US 2004/0149290 published Aug. 5, 2005 (both assigned to Apneon Inc.) describe struts or magnets in the tongue.

II. SUMMARY OF THE INVENTION

According to a preferred embodiment, a method is disclosed for treating obstructive sleep apnea. The method includes identifying a patient with sleep apnea attributable at least in part to movement of a base of a tongue of the patient toward a pharyngeal wall of the patient. A fibrosis-inducing agent is placed within the tongue in a region extending substantially from a hyoid bone rearward toward a back surface of the tongue and upwardly along the back wall toward a free end of a soft palate of the patient.

III. BRIEF DESCRIPTION OF THE DRAWINGS

IV. DESCRIPTION OF THE PREFERRED EMBODIMENT

With reference now to the various drawing figures in which identical elements are numbered identically throughout, a description of the preferred embodiment of the present invention will now be provided.

Figure 1:
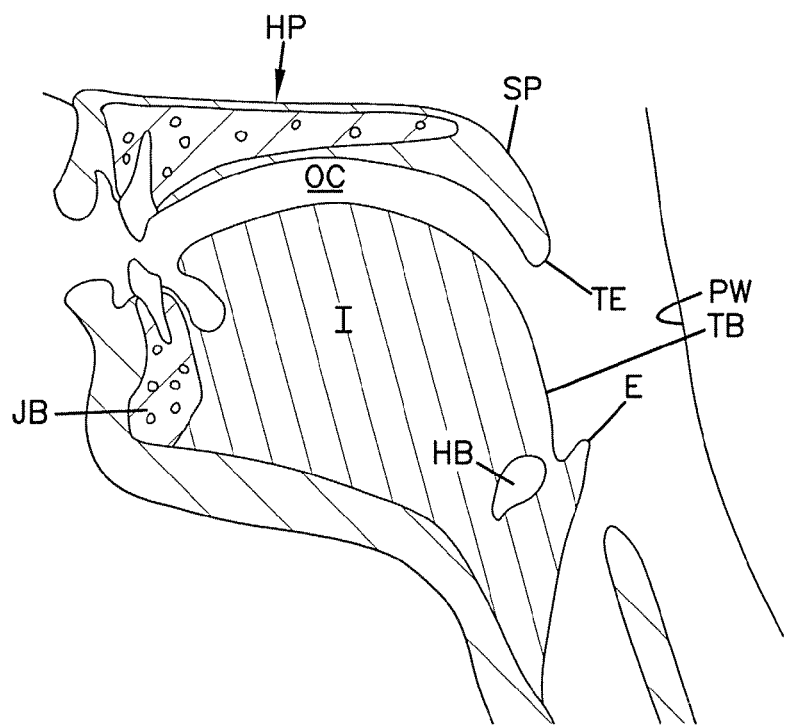
FIG. 1 is a schematic side elevation view of normal anatomy showing the upper airway of the patient and a hyoid bone.

FIG. 1 is a schematic representation of an upper airway of a patient. FIG. 1 shows the tongue T with a tongue base TB opposing a pharyngeal wall PW. The hard palate HP and soft palate SP reside over the top of tongue T with the soft palate SP extending rearward to a trailing end TE between the tongue base TB and the pharyngeal wall PW. A hyoid bone HB resides near the bottom of the tongue near an epiglottis E. A mandible or jaw bone JB is at the front of the tongue T.

Figure 2:
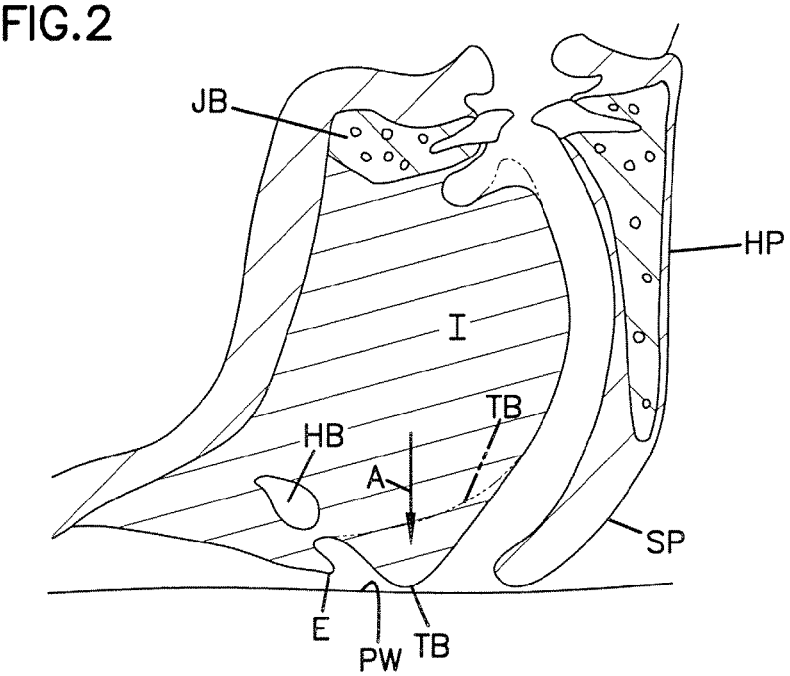
FIG. 2 is the view of FIG. 1 rotated 90 degrees showing, in exaggerated manner, the tongue base falling downward toward a pharyngeal wall.

When reclining during sleep, the tongue base may, in response to gravity or airflow, drop down in closer approximation to the pharyngeal wall. This is illustrated in FIG. 2 where the dotted lines illustrate the positioning of the tongue in FIG. 1 and the solid lines represent the displacement of the tongue in response to gravity with the tongue moving downwardly towards the pharyngeal wall in the direction of the arrow A.

Figure 3:
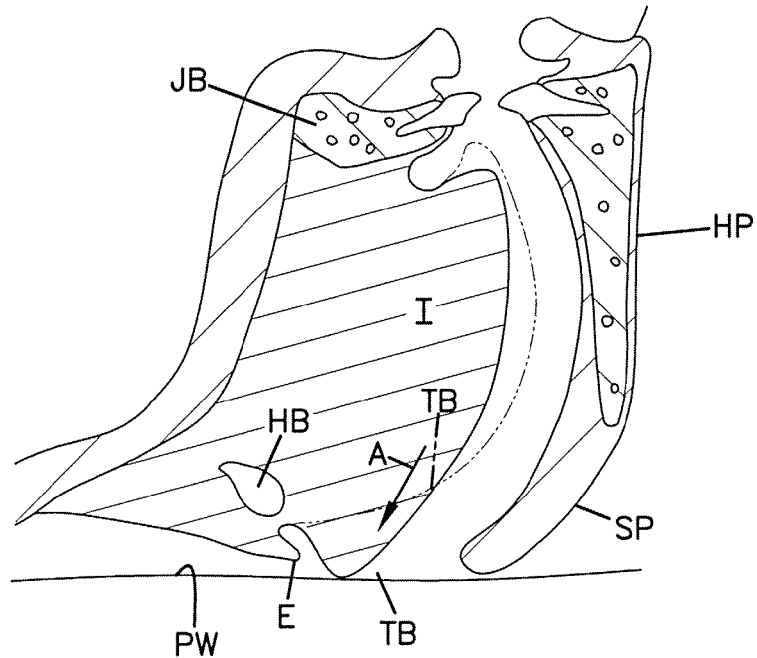
FIG. 3 is the view of FIG. 2 showing a rotation of the tongue base in the event the tongue base is stiffened but not anchored to the hyoid bone.

Various techniques have been suggested for stiffening the base of the tongue. However, if the tongue base is stiffened but not otherwise secured, the tongue base TB continues to move toward the pharyngeal wall in a rotating manner indicated by the arrow A' relative to the hyoid bone HB as illustrated in FIG. 3.

Figure 4:
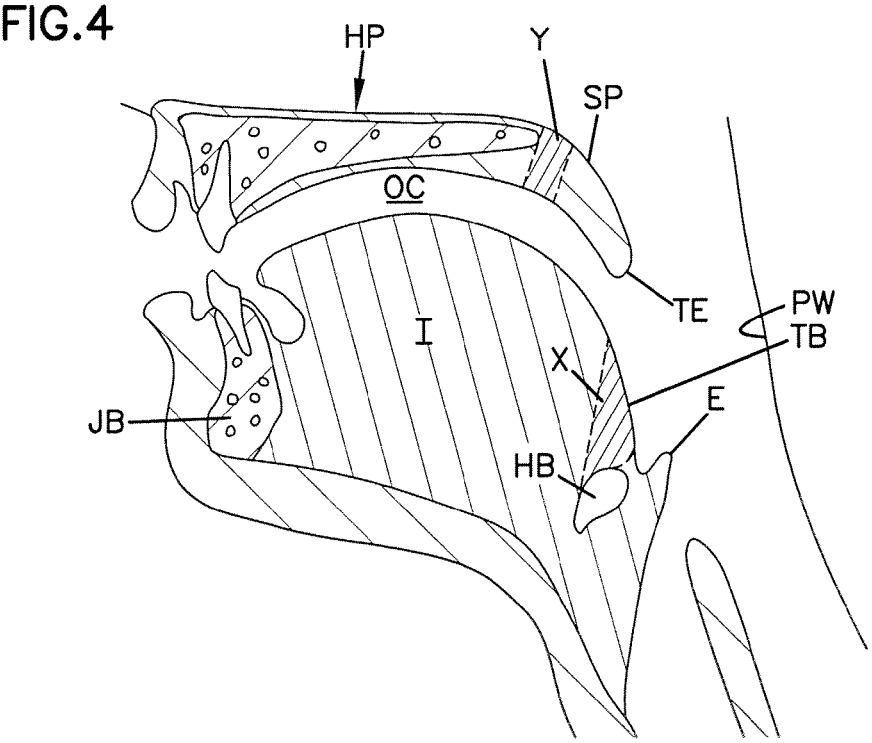
FIG. 4 is the view of FIG. 1 showing a region of the tongue to be stiffened according to the present invention.

The present invention stiffens the tongue base in a manner to create a stiffened area which is anchored to the hyoid bone HB. This is schematically illustrated in FIG. 4 where an area to be stiffened is indicated by X. The area X extends substantially from the hyoid bone rearward towards a back surface of the tongue and upwardly along a back wall of the tongue toward a free end of the soft palate. This region extends laterally superior to the hyoid bone and preferably includes an area including the genioglossus muscle in the region of the hyoid bone.

Figure 5:
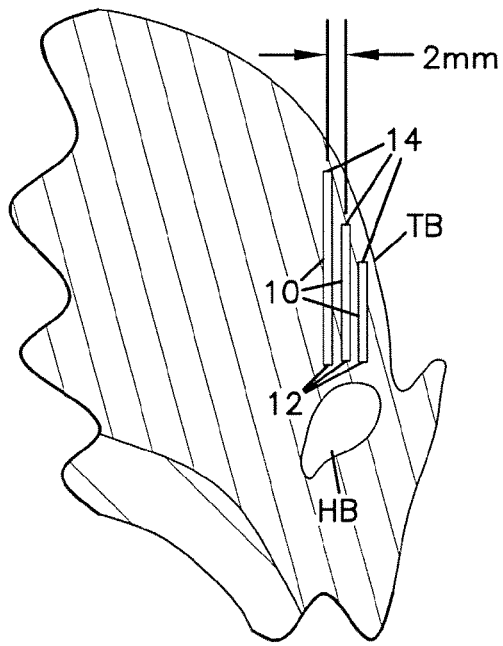
FIG. 5 is a view of a portion of the view of FIG. 4 and showing implants within the base of the tongue to stiffen the tongue.
Figure 7:
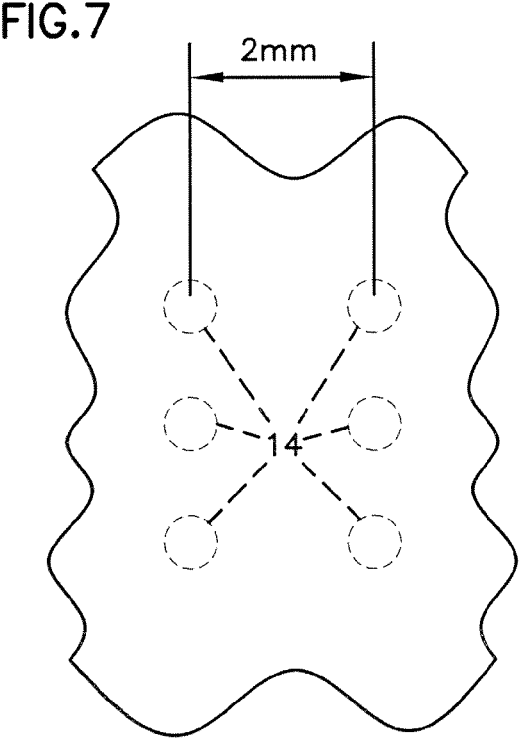
FIG. 7 is a view of the back of the tongue and illustrating, in phantom lines, the placement of the implant of FIGS. 5 and 6.

FIG. 5 illustrates a first embodiment for stiffening the region X. In the embodiment of FIG. 5, a plurality of fibrosis-inducing implants 10 are placed within the region X with one end in close proximity to the hyoid bone and extending longitudinally away from the hyoid bone towards the surface of the tongue base. Preferably such implants 10 are polyester braids such as Pillar® implants of Restore Medical, Inc., St. Paul, Minn., USA. Such implants are approximately 2 millimeters in diameter and about 18 mm in length formed of air textured and braided polyester fibers which induce a fibrotic response after implantation into tissue. Such implants are described in commonly assigned U.S. Pat. No. 6,513,530 to Brenzel et al. issued Feb. 4, 2003 and incorporated herein by reference. Preferably, the implants 10 are placed with their axes approximately 2 millimeters apart as illustrated in FIG. 7. A first end 12 of the implants 10 is placed approximately 2 millimeters from the hyoid bone HB such that the fibrosis induced by the implants overlaps as well as overlaps with the hyoid bone thereby anchoring the fibrosed area and the implants to the hyoid bone. The implants 10 are placed within area X in FIG. 4.

Figure 6:
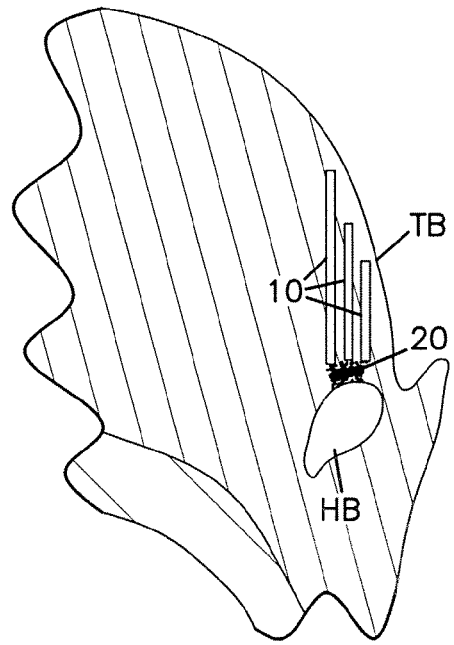
FIG. 6 is the view of FIG. 5 with the addition of a bone-inducing agent between the hyoid bone and the implants of FIG. 5.

FIG. 6 illustrates an enhanced version of the embodiment of FIG. 5 in which a bone-inducing substance 20 is positioned between the hyoid bone HB and the first end 12 of the implants 10. Such a substance causes controlled calcification in the soft tissue and ossification to increase the stiffness of implanted tissue area X and increase the size of the hyoid bone HB. Materials suitable for this purpose are well known bioglasses, hydroxyl appetites, polymeric materials and the like which have a nidus or chelating site for initiation of calcification. Other materials include transforming growth factor beta (TGFb) and cytokines and mediators. Further, NSAIDS and aspirin may be used to modulate and regulate fibrotic response. Such TGFb which if inhibited reduces scarring. It may be incorporated into the Pillar® implants 10 or other implants to increase the rate and amount of scar tissue formation.

The use of such calcification or ossification may also be applied to the hard palate HP in the regions of the soft palate (area Y in FIG. 4) which are not normally calcified or ossified. Also, such material may be placed in close proximity to the hyoid bone without implants 10. Such procedures increase the effective size of such bones HB, HP in order to decrease the motion of the tongue or soft palate by effectively decreasing mobility of the proximal soft or muscular tissue around the bones HB, SP. The placement of such elements may be either by injection of particles which have a propensity to calcify or induce calcification or to be osseo-inductive or to the use of a solid or woven device which has incorporated into its structure or in proximity to its structure materials, as described above, which induce calcification or are osseo-inductive.

The use of the forgoing materials may include scarring or disruption of the periostium in order to accelerate the healing process which would then incorporate implanted materials. Further, this method can be used to induce the growth or formation of cartilage by the selection and placement of materials such that capsule formation around the implanted materials forms a cartilaginous or a fibro-cartilaginous type tissue and which may include the use of specific growth factors such as TGFb or BMF.

Figure 8:
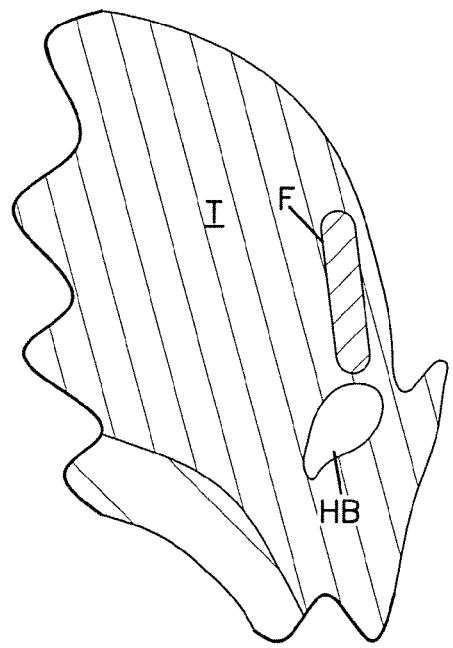
FIG. 8 is the view of FIG. 5 with particulates material substituted for the implant in FIG. 5.

FIG. 8 shows an alternative embodiment to that of FIG. 5. In FIG. 8, a field F of microbeads replaces the location of the Pillar® implants 10 of FIG. 5 in the area X of FIG. 4. The microbeads or other particulate matter may be such as those described in U.S. Pat. No. 6,431,174 to Knudson et al. issued Aug. 13, 2002 and incorporated herein by reference.

Figure 9:
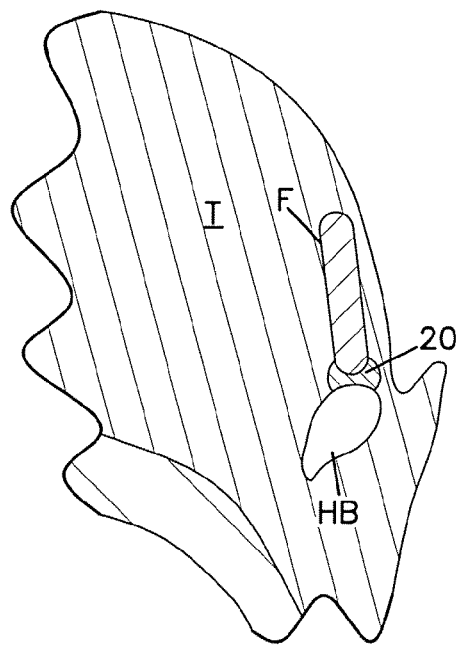
FIG. 9 is the view of FIG. 8 with a bone-inducing agent disposed between the hyoid bone and the particulate field of FIG. 8.
Figure 10:
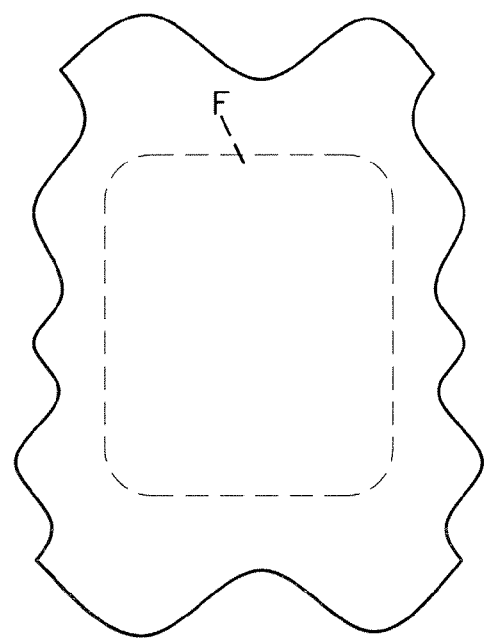
FIG. 10 is a view of a back of the tongue showing the area of particulate material.
Figure 16:
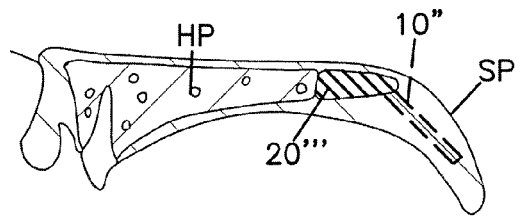
FIG. 16 is a view of the hard and soft palates of FIG. 1 with a bone-inducing agent at a trailing end of the hard palate.

FIG. 9 illustrates an alternative embodiment to that of FIG. 8 in which the calcification material 20 described with reference to FIG. 6 is implanted into the tongue between the hyoid bone HB and the field F of particulate material. FIG. 10 illustrates the field F of particulate material when viewed from the tongue base.

Figure 11:
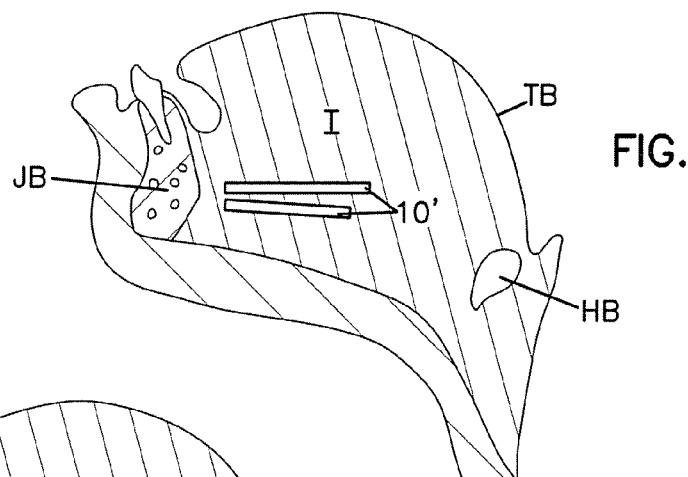
FIG. 11 is the view of the tongue of FIG. 1 with implants extending from a jaw bone toward the hyoid bone.
Figure 12:
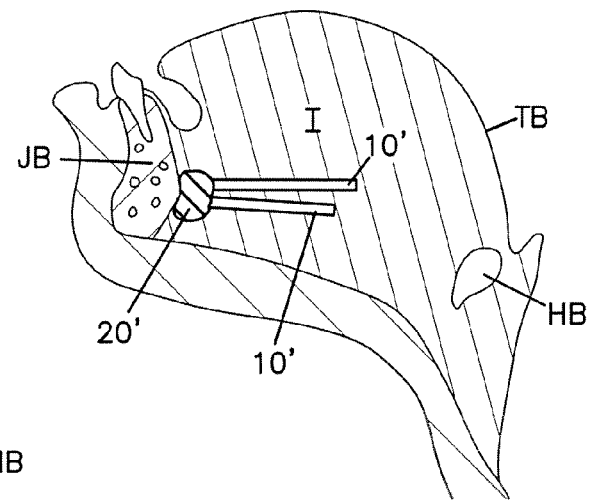
FIG. 12 is the view of FIG. 11 with a bone-inducing agent disposed between the jaw bone and the implants.
Figure 15:
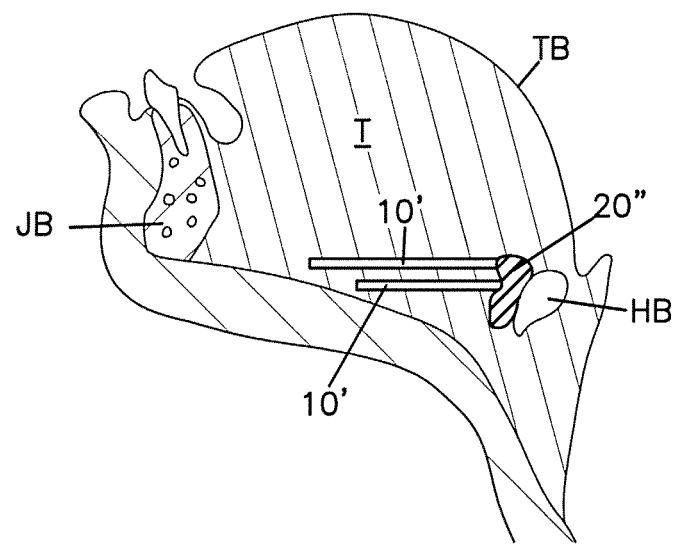
FIG. 15 is the view of FIG. 12 with the bone-inducing agent disposed between the hyoid bone and the implants.

FIG. 11 illustrates a further embodiment where elongated implants 10' are placed extending in an anterior-posterior direction between the jaw bone JB and the region of the hyoid bone HB. The implants 10' are the same construction as implants 10 but preferably longer to extend between the bones JB and HB. In FIG. 12, a calcification material 20' is disposed between the jaw bone JB and a front end of the implants 10'. In FIG. 15, the calcification material 20" is between the rear end of the implants 10' and the hyoid bone.

Figure 13:
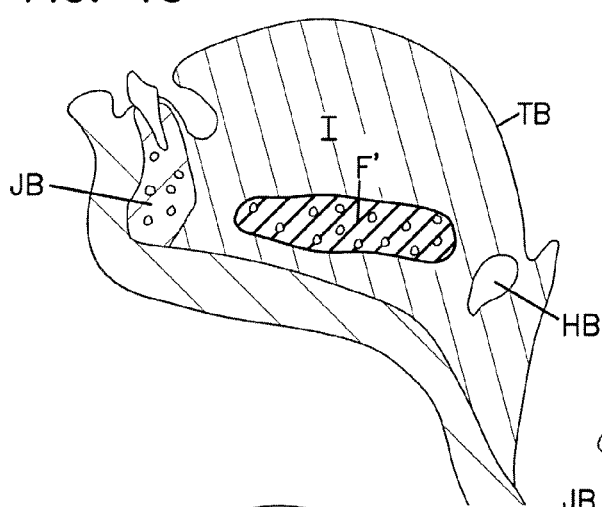
FIG. 13 is the view of FIG. 11 with a particulate field replacing the implants of FIG. 11.
Figure 14:
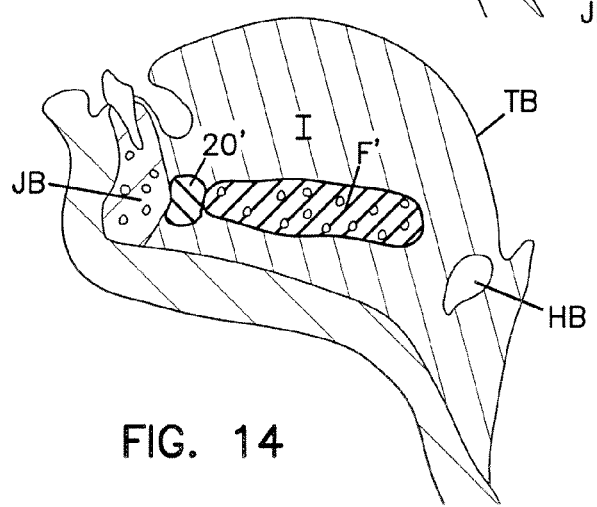
FIG. 14 is the view of FIG. 13 with a bone-inducing agent disposed between the jaw bone and the particulate field.

FIGS. 13 and 14 are similar to FIGS. 11 and 12 except that the implants 10' of FIGS. 11 and 12 are replaced with a field F' of particulate material as earlier described. If desired, the calcification material 20' of FIG. 14 can be placed between the field F' and the hyoid bone HB as described with reference to FIG. 15.

FIG. 15 illustrates use of a calcification material 20''' can treat the soft palate SP to treat obstructive sleep apnea or snoring. The material 20''' is placed in the soft palate SP at the trailing end of the hard palate HP to effectively extend the hard palate HP and thereby stiffen the soft palate SP. An implant 10'' (shown in phantom lines) can be placed in the soft palate SP to further stiffen the soft palate. Implant 10" can be replaced with a particulate field as previously described.

While the fibrosis-inducing agent has been described as a polyester braided implant or field of particulate matter, the fibrosis-inducing agent can be any material suitable for implantation in tissue and known to induce fibrosis. An example of such can include a knit or woven mesh of PET or the like. A sheet material of ePTFE or felt is described in U.S. Pat. No. 6,523,542 to Metzger et al. Issued Feb. 25, 2003 (incorporated herein by reference).

It has been shown how the present invention has been obtained in a preferred embodiment. Modifications and equivalents of the disclosed concepts are intended to be included within the scope of the claims which are appended hereto.

What is claimed is:

1. A method for treating obstructive sleep apnea comprising:
   identifying a patient with sleep apnea attributable at least in part to movement of a base of a tongue of said patient toward a pharyngeal wall of said patient;
   placing an implant within said tongue in a region of said tongue that extends laterally superior to a hyoid bone, said region extending substantially from said hyoid bone of said patient rearward toward a back surface of said tongue, said implant including a fibrosis-inducing agent and an anchor, said fibrosis-inducing agent being anchored to said hyoid bone by said anchor;
   wherein said implant is located entirely within said region of said tongue.

* * * * *